United States Patent
Baudino et al.

(10) Patent No.: US 9,152,769 B2
(45) Date of Patent: Oct. 6, 2015

(54) SYSTEM AND A METHOD FOR DETECTING AN ENDEMIC OR AN EPIDEMIC DISEASE

(75) Inventors: Franck Baudino, Neuilly sur Seine (FR); Laurent Baudino, Paris (FR)

(73) Assignees: Franck Baudino, Neuilly-sur-Seine (FR); Laurent Baudino, Paris (FR); Laurent Filippi, Neuilly-sur-Seine (FR); H4D INTERNATIONAL S.A., Luxembourg (LU)

( * ) Notice: Subject to any disclaimer, the term of this patent is extended or adjusted under 35 U.S.C. 154(b) by 717 days.

(21) Appl. No.: 12/283,428

(22) Filed: Sep. 11, 2008

(65) Prior Publication Data

US 2009/0137882 A1  May 28, 2009

(30) Foreign Application Priority Data

Sep. 11, 2007  (WO) ................ PCT/FR2007/051906

(51) Int. Cl.
*A61B 5/00* (2006.01)
*G06F 19/00* (2011.01)

(52) U.S. Cl.
CPC .......... *G06F 19/3493* (2013.01); *A61B 5/0002* (2013.01); *A61B 5/6888* (2013.01); *G06F 19/34* (2013.01); *A61B 2560/0242* (2013.01)

(58) Field of Classification Search
CPC . G06F 19/3493; G06F 19/322; G06F 19/325; G06F 19/345; G06F 19/3487; G06F 19/363; G06F 19/3418; G06F 19/366; G06F 3/0484; G06Q 50/24; G06Q 50/22; A61B 5/0002; A61B 5/6888; A61B 2560/0242
See application file for complete search history.

(56) References Cited

U.S. PATENT DOCUMENTS

| | | | | |
|---|---|---|---|---|
| 5,410,297 A | * | 4/1995 | Joseph et al. | 340/573.7 |
| 5,448,991 A | | 9/1995 | Polson et al. | 600/330 |
| 5,544,649 A | | 8/1996 | David et al. | |
| 5,619,991 A | * | 4/1997 | Sloane | 600/300 |
| 5,911,132 A | * | 6/1999 | Sloane | 705/3 |
| 5,938,594 A | * | 8/1999 | Poon et al. | 600/300 |
| 6,238,337 B1 | * | 5/2001 | Kambhatla et al. | 600/300 |
| 6,345,195 B1 | * | 2/2002 | Herskowits et al. | 600/473 |
| 6,468,210 B1 | * | 10/2002 | Iliff | 600/300 |
| 6,475,143 B2 | * | 11/2002 | Iliff | 600/300 |
| 6,524,241 B2 | * | 2/2003 | Iliff | 600/300 |
| 6,527,713 B2 | * | 3/2003 | Iliff | 600/300 |
| 6,569,093 B2 | * | 5/2003 | Iliff | 600/300 |

(Continued)

FOREIGN PATENT DOCUMENTS

| | | |
|---|---|---|
| DE | 44 39 080 A1 | 9/1996 |
| FR | 2462584 | 2/1981 |

(Continued)

OTHER PUBLICATIONS

Vishay "Ambient Light and Electromagnetic Interference" Sep. 20, 2006 (document is attached).*

*Primary Examiner* — William Thomson
*Assistant Examiner* — Shirley Jian
(74) *Attorney, Agent, or Firm* — Hamre, Schumann, Mueller & Larson, P.C.

(57) ABSTRACT

This system of detecting endemic or epidemic diseases includes an analysis center connected by a computer network to a number of health booths in which health data can be measured and stored with the conditions under which the measurements are taken. The analysis center generates an alert automatically if an endemic or epidemic disease is detected.

19 Claims, 3 Drawing Sheets

(56) References Cited

U.S. PATENT DOCUMENTS

| | | | |
|---|---|---|---|
| 6,942,625 B1 | 9/2005 | Bryant | 600/538 |
| 7,024,370 B2* | 4/2006 | Epler et al. | 705/3 |
| 7,038,588 B2* | 5/2006 | Boone et al. | 340/573.1 |
| 7,149,756 B1* | 12/2006 | Schmitt et al. | 1/1 |
| 8,160,836 B2* | 4/2012 | Pompei et al. | 702/131 |
| 8,577,642 B2* | 11/2013 | Pompei et al. | 702/131 |
| 8,647,270 B2 | 2/2014 | LeBoeuf et al. | |
| 2002/0002325 A1* | 1/2002 | Iliff | 600/300 |
| 2002/0013515 A1* | 1/2002 | Iliff | 600/300 |
| 2002/0196141 A1* | 12/2002 | Boone et al. | 340/540 |
| 2004/0125996 A1 | 7/2004 | Eddowes et al. | |
| 2005/0101884 A1* | 5/2005 | Weeks et al. | 600/587 |
| 2009/0083066 A1* | 3/2009 | Bailey et al. | 705/2 |
| 2009/0167838 A1* | 7/2009 | Poisner et al. | 348/14.04 |

FOREIGN PATENT DOCUMENTS

| | | |
|---|---|---|
| FR | 2588645 | 4/1987 |
| WO | WO 87/02413 | 4/1987 |

* cited by examiner

SYSTEM AND A METHOD FOR DETECTING AN ENDEMIC OR AN EPIDEMIC DISEASE

BACKGROUND OF THE INVENTION

The field of the invention is that of detecting endemic or epidemic diseases.

The term epidemic refers to the rapid onset of a pathology in a given place during a given time period, not necessarily with any notion of contagion.

An endemic disease, characterized by its habitual presence in a geographical area, can develop into an epidemic if environmental conditions allow.

At present, in an epidemic, doctors send the relevant health authorities information on the increase in the number of cases in an area during a given period.

Doctors are sometimes designated to track a particular pathology. This applies in particular in France for detecting influenza.

Consequently, detection of the epidemic by the health authorities requires collecting numerous case studies and long delays, to the extent that, when an alert is finally issued, the disease has broken out and many people have already become infected.

It is therefore not possible at present to intervene in a preventative manner as soon as an epidemic is suspected.

OBJECT AND SUMMARY OF THE INVENTION

The present invention aims to eliminate the above problems.

To this end, the invention consists in a system for detecting endemic or epidemic diseases, including a cell covering a particular geographical area and including:
- a plurality of health booths installed in the area and connected via a telecommunications network to a remote analysis center, each health booth including:
  - a shell;
  - at least a chair;
  - means for measuring data relative to the health of a user;
  - means for determining, at the time of taking a measurement, one or more conditions under which the measurement is taken;
  - means for storing the measured data in a data structure together with the condition(s) under which the measurements were taken; and
  - means for sending the data structure to the remote analysis center via the network;
- the remote analysis center including:
  - means for receiving the data structures sent by the health booths;
  - a database including:
    - a range of "normal" values for each type of data; and
    - a range of "interpretable" values for each type of measurement condition;
  - means for calculating:
    - the number of data structures including interpretable measurement conditions received during a particular time period, and in those structures:
    - the percentage of abnormal data, i.e. data outside the range of normal values, for each type of data; and
  - means for triggering an alert via the network if:
    - the number of data structures is above a particular threshold; and
    - the percentage of abnormal data for one or more types of data is above a particular threshold;
    - the type of alert being chosen as a function of the number of types of data for which the percentage of data is abnormal.

In a correlated way, the invention consists in a method of detecting endemic or epidemic diseases, including:
- installing one or more cells covering a particular geographical area and including a number of health booths installed in the area and connected via a telecommunications network to a remote analysis center;
- taking measurements in the health booths of data relating to the health of a user and determining at the time of taking the measurements one or more conditions under which the measurements are taken, the measured data being stored in a data structure together with the conditions under which the measurements are taken;
- sending the data structures from the health booths to the remote analysis center via the network, the remote analysis center including a database including:
  - a range of "normal" values for each type of data; and
  - a range of "interpretable" values for each type of measurement condition;
- calculation by the remote analysis center of:
  - the number of data structures including interpretable measurement conditions received during a particular time period and, in those structures:
  - the percentage of abnormal data, i.e. data outside the range of normal values, for each type of data; and
- triggering an alert via the network if:
  - the number of data structures is above a particular threshold; and
  - the percentage of abnormal data for one or more types of data is above a particular threshold;
- the type of alert being chosen as a function of the number of types of data for which the data percentage is abnormal.

Accordingly, a general aim of the invention is to propose detecting endemic and epidemic diseases by using a computer network to connect a plurality of health booths in which health data can be measured and stored in association with the conditions under which the measurements are taken to a remote analysis center adapted to manage an alert automatically if an endemic or epidemic disease is detected.

A health booth of the invention is primarily for obtaining measurements establishing the health of a user and for sending those measurements to the analysis center.

The health booths can also display general or personalized alert messages if an epidemic or endemic disease is detected.

The health booths are preferably installed in busy places, to ensure effective territorial coverage.

For example, a health booth covers at least 1 km$^2$ and/or an average population of 1000 persons.

In one particular embodiment of the invention, the system can include cells covering contiguous geographical areas, their analysis centers sending the data structures to a centralized management center that can aggregate the data over a large geographical area, for example the size of a town.

Establishing a person's health requires a number of measurements (weight, heart rate, temperature, etc.) to be taken under the supervision of medical personnel.

These measurements must sometimes be repeated at regular intervals to track how they change over time.

The obligatory presence of health personnel causes a number of problems.

First of all, it is clear that in developing countries, where the density of health personnel is low, it is difficult to conduct a health campaign, especially in an emergency, where there is an epidemiological risk present.

In other regions, the main impediment to health screening individually or collectively on a large scale is the relatively high cost of the presence of the above-mentioned health personnel.

To limit the above-mentioned problems, there are known, in particular from the document U.S. Pat. No. 5,554,649, "telemedicine" methods in which patients communicate with a doctor or other health personnel remotely, via a telecommunications network, the patients themselves effecting a number of measurements that are sent to the doctor via the network.

It should be noted that those solutions are not really satisfactory since they require the presence of health personnel when the measurements are taken, even though at a remote location.

One solution that springs naturally to mind would be to have patients take the measurements themselves, for example at home, with no contact with medical personnel, and then send the measurements to a remote center for subsequent processing.

However, it is difficult to envisage such a procedure since it is known that medical measurements are strongly linked to the conditions under which they are taken, in particular the patient's stress or fatigue and the meteorological, sound, and light environment at the time of taking the measurements.

In other words, if this information is not known, the measurements cannot be used by a doctor with sufficient reliability.

The detection system and method of the invention are therefore particularly advantageous in that they enable patients' health data to be collected without intervention of doctors, interpretation of the data by the remote analysis center being reliable because it takes account of the environmental conditions under which the measurements were effected.

In the context of the invention, the expression "health booth" must be interpreted broadly, and designates any space defined by a shell in which users can themselves make a number of measurements relating to their health without the presence of medical personnel being necessary, even at a remote location.

A health booth in the sense of the invention can be transportable, for example, so that it can be installed temporarily at a given location. Health booths in the context of the invention can in particular consist of mobile homes or vehicles of the type used for collecting blood from donors.

A health booth in the context of the invention can also consist of a fixed structure intended to be installed in places through which people pass, for example airports or hotels.

The health booth can be connected to the remote analysis center by any type of telecommunications network, for example a GSM, GPRS, UMTS, etc. wireless telecommunications network.

It is particularly advantageous if the remote analysis center takes account only health data measured under acceptable conditions in order to detect epidemic or epidemiological diseases.

Consequently, the database of the remote analysis center is essential since it makes it possible to determine whether the data relating to the health of a patient should or should not be retained in the detection process.

In the present document the expression "range of values that are interpretable" refers to the conditions under which measurements need to be taken in order to ensure the health measurement data is meaningful and therefore retained.

In one embodiment of the invention, the process of detecting epidemic and epidemiological diseases discards health measurements not taken under the following conditions:
  temperature in the range 17° C. to 25° C.;
  relative humidity in the range 10% to 30%; and
  brightness in the range 100 cd to 140 cd.

Consequently, when the remote analysis center receives a data structure in which one or more measurement conditions departs from one of the above ranges, that structure is not retained for detection of endemic or epidemic disease.

Generally speaking, the remote analysis center seeks to detect patients presenting with abnormal health data.

Consequently, the database of the remote analysis center includes a range of "normal" values for each type of data, which values correspond to the values for a patient in good health.

For example, the following data is considered to be typical of a patient in good health:
  blood oxygen saturation in the range 97% to 100%;
  systolic arterial pressure in the range 110 mmHg to 140 mmHg;
  diastolic arterial pressure in the range 65 mmHg to 90 mmHg;
  temperature in the range 36.5° C. to 37.5° C.;
  heart rate in the range 60 bpm to 80 bpm; and
  body mass index BMI in the range 19 to 29.

Other measurement conditions can be recorded, of course, and in particular the position of the user, which greatly influences the measured blood pressure. It is recommended that blood pressure is measured in a seated position, the arm resting on a table and the inflatable cuff positioned on that arm at the same level as the heart.

It is also known that the measured blood pressure is greatly influenced by events liable to increase it, in particular cold, noise, and physical effort.

It is also known that environmental stress and hyperthermia greatly influence the heart rate.

It is also known that the blood oxygen saturation level is greatly influenced by the ambient light level and by the relative humidity to which the skin is exposed.

Generally speaking, the means for measuring the above data can consist of appropriate sensors combined with calculation means.

For example, to be sure that a user is seated comfortably when taking blood pressure, it can be envisaged to use pressure sensors placed on the seat and on the backrest of the chair in the health booth.

To be sure that the user's arm is resting in an appropriate position, sensors can be placed on an armrest of the chair in the health booth.

A thermometer, a microphone, a hygrometer, and a photoelectric cell can be used to measure the temperature, sound level, relative humidity and brightness inside or outside the shell.

In a preferred embodiment of the invention a health booth includes means for verifying that health measurements are taken when a given condition satisfies one or more predetermined criteria.

This feature means that health measurements can be effected under optimum conditions.

For example, it can be decided not to measure blood pressure until the patient has been seated for at least five minutes.

In one embodiment of the invention, these control means are optional because it can be important, especially after a natural disaster, to take large numbers of health measurements, in order to implement emergency measures, even though the measurement conditions are below optimum.

In other embodiments, the control means can be used systematically.

The shell of the health booth used in a preferred embodiment of the invention includes one or more openings for linking the health booth to one or more other health booths.

This forms a "hospital" consisting of interconnected health booths.

This feature proves particularly advantageous for guaranteeing certain predetermined conditions in a number of health booths installed in the same area.

For example, in a particularly hot region, it is easier to reduce the temperature in a number of health booths that communicate with each other than in the same number of individual health booths.

The health booth used in one preferred embodiment of the invention includes power supply means.

These power supply means can use solar energy, for example, or open and/or closed thermodynamic cycles. They are used to supply the health booth with electricity and to regulate the temperature inside the health booth.

For more details of such power supply means, the person skilled in the art can refer to the patent documents FR 2 462 584 and FR 2 588 645.

In one particular embodiment of the invention, each user is associated with a unique identifier preserving their anonymity.

This unique identifier can be generated at random, for example.

In one particular embodiment of the invention, this unique identifier is delivered by a health booth, for example by means of a ticket the first time the user uses a health booth.

This ticket can include a bar code that is read by a reader installed in the health booths before each subsequent use of a health booth, for example.

Alternatively, users can enter their identifier by means of a keypad or a touch-sensitive screen installed in the health booth.

The identifier of the user is preferably sent to the remote analysis center with the user's health data and the conditions under which the measurements were taken, and the remote analysis center preferably includes means for storing a user's health data in a server with their identifier.

In one particular embodiment of the invention, the remote analysis center systematically stores the health data of a patient, even if the data is acquired under measurement conditions that cannot be interpreted.

Be this as it may, by means of the anonymous identifier, a user can subsequently access their personal data on the server via a network, for example via the Internet.

According to the invention, the remote analysis center of the invention can trigger various types of alert.

For example, a first level alert can send a message to the health authorities if health data that departs from the normal conditions is detected in a given geographical area during a given time period.

For example, if a blood oxygen saturation level less than 97% is detected over a period of seven days for a population of at least one hundred persons, a message including that information can be sent to the health authorities, who are then in a position to interpret this phenomenon as the spread of a respiratory problem.

In one particular embodiment of the invention, if two parameters depart from their normal ranges of values, the alert can individually warn each user presenting with those abnormal parameters shortly after they take the measurements, for example by means of a screen in the health booth.

For example, if a temperature higher than 38° C. is detected for the above-mentioned population, a personal message can be sent to a user prompting them to contact their doctor, this abnormally high temperature, in combination with the blood oxygen saturation level, undoubtedly being a symptom of a respiratory infection.

For example, if at least the following parameters are detected: high heart rate, abnormal blood oxygen saturation level and abnormal temperature, a respiratory pathology alert message could be sent to the health authorities, in addition to displaying personalized information on the screen in the health booth.

The invention can also detect the outcome of epidemics over longer periods, for example three years.

For example, if a remote analysis center detects from the weight/height ratio a body mass index greater than 30, an obesity epidemic alert could be sent to the relevant authorities and a dietary message targeted to health booths in the area in which the pathology has appeared.

Moreover, if at least the following parameters are detected: abnormal blood pressure, high heart rate, and high body mass index, a cardiological alert message can be sent to the health authorities, which authorities can then broadcast information messages in the geographical area concerned to request those living there to avoid running at the end of the afternoon.

BRIEF DESCRIPTION OF THE DRAWINGS

Other features and advantages of the present invention emerge from the following description with reference to the drawings, which show a non-limiting embodiment of the invention, and from appendix 1. In the figures.

Figure 2:
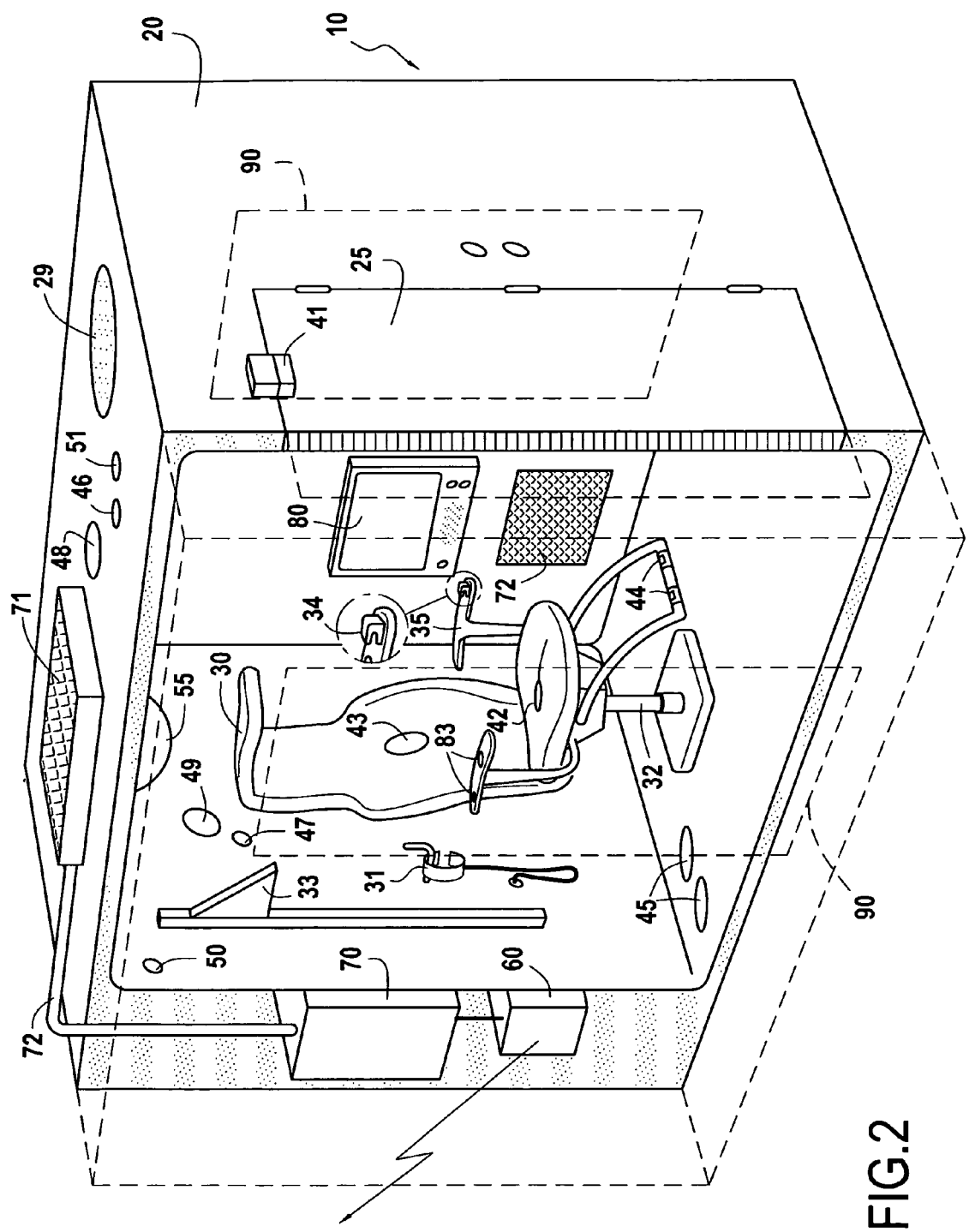
FIG. 2 shows a health booth conforming to one particular embodiment of the invention.

Appendix 1 gives one example of a data structure generated by the FIG. 2 health booth.

DETAILED DESCRIPTION OF ONE EMBODIMENT

Figure 1:
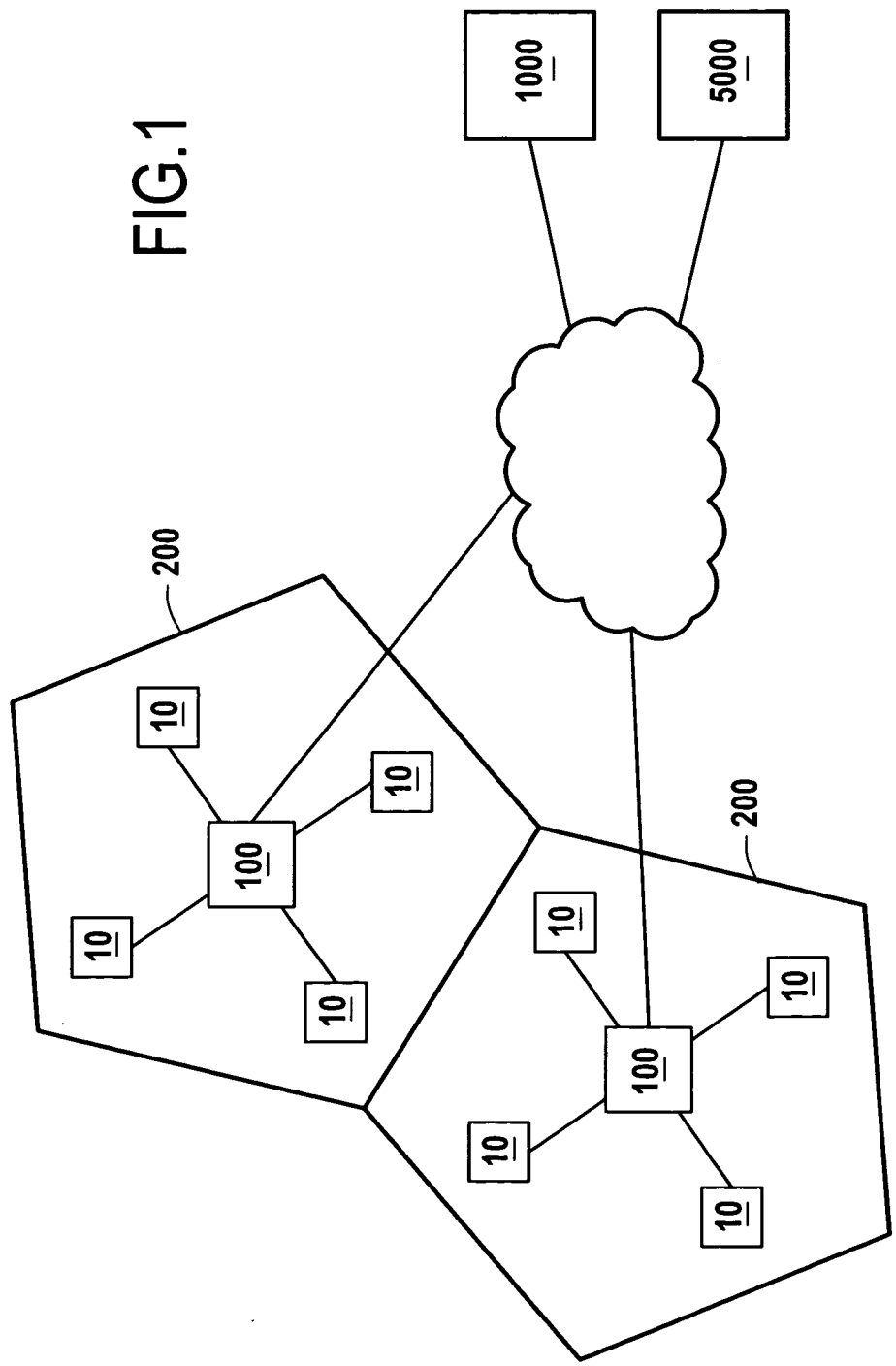
FIG. 1 represents a detection system of the invention.

FIG. 1 represents a detection system conforming to one particular embodiment of the invention.

This system includes a plurality of cells 200, each cell including four health booths 10 connected via a telecommunications network to a remote analysis center 100.

The remote analysis centers 100 send data structures received from the health booths 10 to a central management system 1000.

In the embodiment described here, the data structures sent by the health booths include an identifier of the user, each identifier being unique and preserving the user's anonymity.

In the embodiment described here, the remote analysis centers store the health data for a user with their identifier in a server 5000.

Users can then access this server, using their identifier, to see their personal medical data.

FIG. 2 represents a health booth 10 that can be used in one particular embodiment of the invention.

The main components of the health booth 10 are a shell 20 and a chair 30.

In a different embodiment of the invention, the health booth 10 can contain a number of chairs 30.

The health booth includes a touch-sensitive screen 80 adapted to:

provide a user with a random unique identifier on their first visit to a health booth 10; and read the unique identifier entered on the touch-sensitive screen by a user on their subsequent visits to a health booth 10.

The health booth 10 includes a number of means for measuring data related to a user's health.

In the embodiment described here, these measuring means comprise:

an inflatable cuff 31 placed on the user's arm to measure their blood pressure, this cuff further including heart rate sensors, not shown;

scales 32 for measuring the user's weight when seated on the chair 30;

a height gauge 33 for measuring the user's height in a standing position; and an oximeter 34 for measuring the user's blood oxygen saturation level.

In the embodiment described here, the oximeter 34 is fixed to the end of one armrest 35 of the chair 30.

According to the invention, the health booth 10 includes a number of sensors for determining the conditions under which the health measurements are taken.

In the embodiment described here, these sensors comprise:

a sensor 41 for determining whether the door 25 of the health booth is open or closed;

a pressure sensor 42 on the seat of the chair 30 for detecting whether the user is seated on the chair;

a pressure sensor 43 in the back rest of the chair 30 for determining whether the user is sitting back in the chair 30;

two sensors 44 on a footrest attached to the chair 30 for detecting whether the user has both feet resting on the footrest;

two sensors 45 disposed under the height gauge 33 to determine whether the user is correctly placed when measuring their height with the height gauge 33 or measuring their blood pressure in the standing position using the inflatable cuff 31;

a thermometer 46 for measuring the temperature outside the shell 20;

a thermometer 47 for measuring the temperature inside the shell 20;

a hygrometer 48 for measuring the relative humidity outside the shell 20;

a hygrometer 53 for measuring the relative humidity inside the shell 20;

a microphone 50 for measuring the sound level inside the health booth 10; and a photo-electric cell 54 for measuring the brightness level outside the shell 20.

In the embodiment described here, the health booth 10 includes a lamp 55 for producing a predetermined brightness inside the health booth 10 so that the brightness inside the shell 20 is the optimum for taking health measurements with the door 25 closed.

When a health measurement is taken, the conditions under which it was taken are stored in a data structure with the measurement results and the unique identifier of the user.

In the example described here, this data structure is a computer file.

Figure 3:
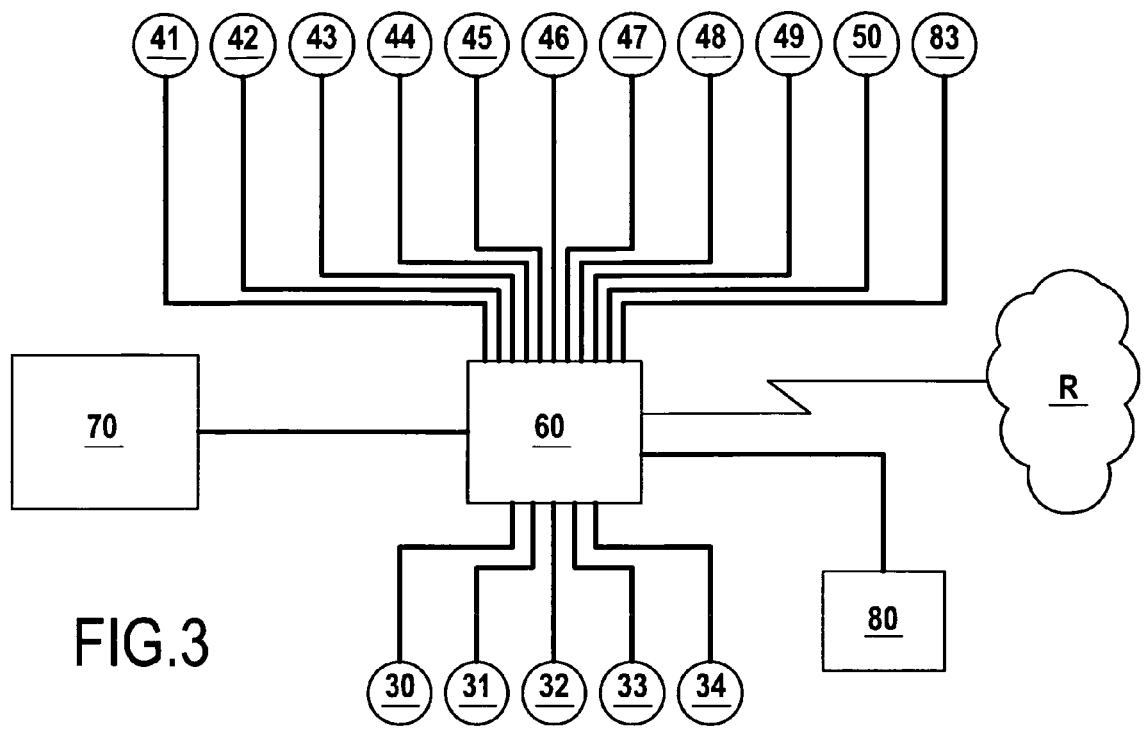
FIG. 3 shows the connections of a computer used in the FIG. 1 health booth.

The health booth 10 includes a computer 60 to which each of the sensors and measuring instruments referred to above is connected, as shown in FIG. 3.

This computer 60 is adapted to generate a file as shown in Appendix 1 and to send that file to a remote analysis center 100 via a telecommunications network R.

In the example described here, the computer 100 is installed within the thickness of the shell 20.

In the particular embodiment described here, the computer 60 and all the electrical equipment of the health booth 10 are supplied with power by a motor 20 placed within the thickness of the shell 20 and connected to a solar panel 71.

The solar panel 71 heats a fluid injected into the motor 70 via a pipe 72, the motor using this heat energy to generate the electrical power supply necessary for the electric instruments of the health booth 10 to operate and to effect cooling by compressing another fluid.

The motor 70 is therefore adapted in particular to regulate the temperature inside the health booth 20 by injecting warm air into it via a grille 72.

The health booth 10 described here also includes a ventilation grille 29.

There is described below a scenario for use of the health booth 10 to establish a health file for a user in the form shown in Appendix 1.

The user enters the health booth 10 via the door 25, leaving the door open behind them, which is detected by the sensor 41.

The touch-sensitive screen 80 shows a message prompting the user to enter their identifier. In this embodiment the health measurements cannot begin until this identifier is entered. The identifier is then stored in the Appendix 1 file.

Once the identifier of the user has been entered, a message on the touch-sensitive screen prompts the user to enter their age and to measure their height using the height gauge 33.

Until the user places their feet correctly on the marks aligned with the sensors 45, a message prompts them to assume a new position.

The height is then stored in the Appendix 1 file.

Once their height has been measured, the user is prompted to remain standing on the above-mentioned marks to measure their blood pressure in the standing position. Sensors in the cuff 31 detect that it is positioned correctly.

When this has been detected, the computer 60 starts a counter and takes two blood pressure measurements, after one minute and after five minutes, respectively, and the respective results 11.8 and 11.6 of these measurements are stored in the Appendix 1 file.

The user is then prompted to sit on the chair 30.

Before measuring their weight, it is verified that the user is seated (sensor 42 activated) with both feet placed on the footrest (position of the feet detected by the sensors 44).

If so, the weight is measured by the scales 32 and stored in the Appendix 1 file (81 kg).

A message on the touch-sensitive screen 80 then prompts the user to put the blood pressure cuff 31 on again to measure their blood pressure in the seated position.

In the embodiment described here, to optimize the blood pressure measurement, the user is required to be seated (this is detected by the sensor 42) and sitting back in the chair 30 (this is detected by the sensor 43) with their arm resting on the armrest 35 (this is detected by two position sensors 83).

When the computer 60 registers this position, it requests the user to wait for five minutes.

In this example, when the five minute delay expires, the user has unfortunately removed their arm from the armrest 35.

The measured blood pressure 12.7 is stored in the data structure, with information representing the fact that the user was seated and sitting back but that their arm was not positioned on the armrest.

At the time of measuring the user's heart rate using the blood pressure cuff 31, the microphone detects a very high noise level, namely a noise level of 120 dB caused by a jackhammer.

It is known that noise level strongly impacts on the heart rate.

Consequently, the touch-sensitive screen 80 prompts the user to close the door 25, which is detected automatically by the sensor 41.

A noise level of 50 dB is then measured inside the health booth 10.

When the door 25 is closed, the lamp 55 produces an optimum brightness level of 120 cd.

When the measurement is taken the temperature inside the health booth is 19° C.

The touch-sensitive screen 80 prompts the user to wait for one minute and a heart rate of 60 bpm is then stored in the Appendix 1 file.

Finally, a message prompts the user to measure their blood oxygen saturation by placing their index finger in the oximeter 34 positioned at the end of the armrest 35.

The measured brightness (120 cd) and relative humidity (4%) are stored with the result of this $SpO_2$ blood oxygen saturation measurement: 95%.

The computer 60 then sends the file automatically to a remote analysis center 100 via a telecommunications network R.

In the embodiment described here, the health booth 10 has two facing removable doors 90.

Figure 4:
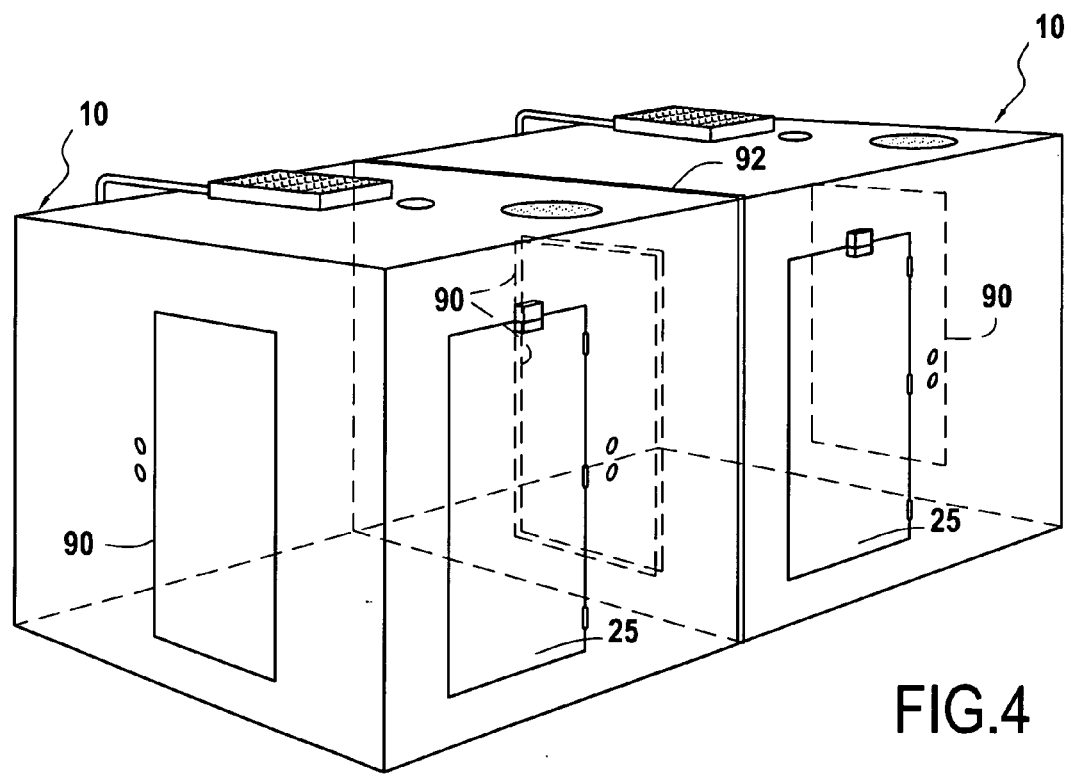
FIG. 4 shows a number of health booths of the invention interconnected to form a hospital.

As shown in FIG. 4, these doors enable a "hospital" to be produced by positioning two health booths side by side and removing the removable doors 90 to create an airlock passage between the two health booths.

In a preferred embodiment, the health booths 10 in this particular arrangement are connected together by an air-tight seal 92.

When the remote analysis center receives the data structures from the health booths, it begins by:
  feeding the information to the central management center 1000; and
  saving the health data in the server 5000 with the unique identifier contained in the data structure.

It then determines whether the data can be used by comparing the measurement taking conditions contained in the data structure with a range of interpretable values for each type of measurement condition.

If one or more measurement conditions depart from the associated range of interpretable values, the remote analysis center does not take the data structure into account to detect epidemic or endemic diseases.

After this filtering, the remote analysis center determines whether each item of data relating to the user's health departs from the range of normal values for that type of data.

Each remote analysis center 100 is therefore able to calculate, over a particular time period:
  the number of data structures including conditions suitable for measurements to be interpretable and, in those data structures:
  the percentage of abnormal data for each type of data.

It can then trigger an alert automatically when storing the physiological data measurements, as soon as abnormalities occur, even before the disease has broken out.

In the embodiment described here, the system of the invention triggers an alert in the case of a respiratory virus, this situation being characterized by:
  a measured temperature above 38.2° C.;
  a blood saturation level below 95%; and
  a heart rate above 90 bpm.

If one or more of these conditions is detected for at least 20% of a population of 100 people, the remote management center 100 sends a message to the health authorities.

If two or more conditions are detected (for example temperature above 38.2° C. and blood saturation level below 95%), the remote management center sends a personalized information message via the telecommunications network to any user presenting with such measurements, to encourage them to consult their doctor, this message being shown on the touch-sensitive screen 80 in the health booth in which the user is located.

APPENDIX 1

| Identifier: | | # 1234 |
|---|---|---|
| Age: | | 30 years |
| Blood pressure | | |
| Seated: | ☑ | 12.7 |
| Sitting back: | ☑ | |
| Arm on armrest: | ☐ | |
| Duration: | 5 min | |
| STANDING: | | |
| 1 min: | | 11.8 |
| 5 min: | | 11.6 |
| Weight | | |
| Seated: | ☑ | 81 kg |
| Feet on footrest: | ☑ | |
| Height: | | 178 cm |
| Heart rate: | | |
| T: | 19° C. | 60 bpm |
| Brightness: | 120 cd | |
| Noise level: | 50 dB | |
| 1 min | ☑ | |
| Blood oxygen saturation | | |
| Brightness: | 120 cd | $SpO_2$ 95% |
| Relative humidity: | 4% | |

The invention claimed is:

1. A system for detecting endemic or epidemic diseases, including a cell covering a particular geographical area and including:
  a plurality of health booths installed in said area and connected via a telecommunications network to a remote analysis center, each health booth allowing a user to conduct self-measurement and comprising:
    a shell;
    a chair;
    a first measurement device configured for a user to measure health data relative to the health of the user;
    a second measurement device configured to determine, at the time of taking a measurement with the first measurement device, one or more environmental conditions of the health booth under which said measurement is taken;
    data storage configured to store said measured health data from the first measurement device in a data structure together with said condition(s) under which the measurements were taken; and a transmission system configured to send said data structure to said remote analysis center via said network;
said remote analysis center comprising:
a receiving system configured to receive said data structures sent by said plurality of health booths;
a database configured to store:
a range of normal values for each type of said health data measured by the first measurement device; and
a range of interpretable values for each type of environmental condition measured by the second measurement device;
a calculator configured to determine:
the number of data structures, sent by the plurality of health booths, that include interpretable environmental conditions received during a particular time period, and in the data structures that include interpretable environmental conditions:
the percentage of abnormal health data for each type of health data; and
an alert trigger configured to trigger an alert via said network if:
said number of data structures is above a threshold; and
the percentage of abnormal data for one or more types of data is above a threshold;
the type of alert being chosen as a function of the number of types of data for which said percentage of data is abnormal.

2. The system according to claim 1, wherein the alert trigger:
is configured to send a message to health authorities if there is one type of data for which said percentage of data is abnormal;
is configured to present to the user of said health booth a message prompting them to consult a doctor if there are two types of data for which said percentage of data is abnormal and if the corresponding health data of the user concerned, as measured under interpretable conditions, is abnormal.

3. The system according to claim 1 wherein said first measurement device is configured to measure and send to the remote analysis center data relating to the health of said user selected from the group consisting of:
the user's blood oxygen saturation, the range of normal values stored in the database of said remote analysis center being the range [97%, 100%];
the user's systolic blood pressure, the range of normal values stored in the database of said remote analysis center being the range [110 mmHg, 145 mmHg];
the user's diastolic blood pressure, the range of normal values stored in the database of said remote analysis center being the range [65 mmHg, 90 mmHg];
the user's heart rate, the range of normal values stored in the database of said remote analysis center being the range [60 bpm, 80 bpm]; and
the user's body mass index, the range of normal values stored in the database of said remote analysis center being the range [19, 29].

4. The detection system according to claim 1, wherein said second measurement device is configured to measure and send to the remote analysis center one or more of the conditions selected from the group consisting of:
the temperature inside said shell, the associated range of interpretable values stored in the database of said remote analysis center being the range [17° C., 25° C.];
the relative humidity inside said shell, the associated range of interpretable values stored in the database of said remote analysis center being the range [10%, 30%]; and
the brightness level inside said shell, the associated range of interpretable values stored in the database of said remote analysis center being the range [100 cd, 140 cd].

5. The system according to claim 1, including a plurality of cells covering contiguous geographical areas, each of the cells comprising an analysis center, the analysis centers of said cells sending said data structures to a centralized management center.

6. The system according to claim 5, including a health booth for each 1 $km^2$ and/or for each 1000 residents and a remote analysis center for every five health booths.

7. The system according to claim 1 wherein:
one or more of said health booths includes a reader configured to read an identifier of said user, which is sent to said remote analysis center in said data structure;
said remote analysis center includes a server configured to store the health data of a user with said identifier;
said identifier preserving users' anonymity and enabling them to access their personal medical data on said server via a network.

8. The system according to claim 1, wherein one or more of said health booths includes a checking system configured to confirm whether said measurements are taken when said environmental condition complies with one or more predetermined criteria.

9. The system according to claim 1, wherein one or more of said health booths include one or more openings for connection to one or more other health booths.

10. The detection system according to claim 1, wherein one or more of said health booths includes a power supply.

11. The system of claim 1, further comprising a system configured to provide the user with instructions for taking the measurement with the first measuring device.

12. A method of detecting endemic or epidemic diseases, comprising:
installing one or more cells covering a particular geographical area and comprising a plurality of health booths installed in said area and connected via a telecommunications network to a remote analysis center;
taking measurements in said plurality of health booths of data relating to the health of a user with a first measurement device configured for the user to measure health data relating to the health of the user, and determining, with a second measurement device, at the time of taking the measurements one or more environmental conditions of the health booth under which said measurements are taken, the measurement being taken by the user in the health booth, the measured data being stored in a data structure with said environmental condition under which said measurements are taken;
sending said data structures from said plurality of health booth to said remote analysis center via said network, said remote analysis center including a database including:
a range of normal values for each type of data; and
a range of interpretable values for each type of environmental condition;
said remote analysis center determining
the number of data structures, sent by the plurality of health booths that include interpretable measurement conditions received during a particular time period and, in the data structures that include interpretable environmental conditions:
the percentage of abnormal data for each type of data; and
said remote analysis center triggering an alert via said network if:

said number of data structures is above a threshold; and
the percentage of abnormal data for one or more types of data is above a threshold;
the type of alert being chosen as a function of the number of types of data for which said data percentage is abnormal.

13. The method according to claim 12, wherein the triggering:
sends a message to health authorities if there is one type of data for which said percentage of data is abnormal;
presents to the user of said health booth a message prompting them to consult a doctor if there are two types of data for which said percentage of data is abnormal and if the corresponding data of that user, measured under interpretable conditions, is abnormal.

14. The method according to claim 12, wherein one or more items of data relating to the health of said user are chosen from the group consisting of:
the user's blood oxygen saturation, the range of normal values stored in the database of said remote analysis center being the range [97%, 100%];
the user's systolic blood pressure, the range of normal values stored in the database of said remote analysis center being the range [110 mmHg, 145 mmHg];
the user's diastolic blood pressure, the range of normal values stored in the database of said remote analysis center being the range [65 mmHg, 90 mmHg];
the user's heart rate, the range of normal values stored in the database of said remote analysis center being the range [60 bpm, 80 bpm]; and
the user's body mass index, the range of normal values stored in the database of said remote analysis center being the range [19, 29].

15. The method according to claim 14, wherein one or more of the environmental conditions is chosen from the group consisting of:
the temperature inside said shell, the associated range of interpretable values stored in the database of said remote analysis center being the range [17° C., 25° C.];
a relative humidity inside said shell, the associated range of interpretable values stored in the database of said remote analysis center being the range [10%, 30%]; and
a brightness level inside said shell, the associated range of interpretable values stored in the database of said remote analysis center being the range [100 cd, 140 cd].

16. The method according to claim 12, wherein a number of cells covering contiguous geographical areas are installed, the cells including a plurality of analysis centers, the analysis centers of said cells sending said data structures to a centralized management center.

17. The method according to claim 12, wherein:
one or more of said health booths includes a reader that reads an identifier of said user, which is sent to said remote analysis center in said data structure;
said remote analysis center stores a user's health data in a server with said identifier;
said identifier preserving anonymity of said user and enabling them to access their personal medical data on said server via a network.

18. The method according to claim 12, wherein one or more of said health booths confirms that said measurement is taken when said environmental condition complies with one or more predetermined criteria.

19. The method of claim 12, further comprising instructing the user as to taking the measurements.

* * * * *